United States Patent [19]

Cooper

[11] Patent Number: 4,902,698
[45] Date of Patent: Feb. 20, 1990

[54] BENZENESULPHONAMIDOPYRIDYL COMPOUNDS WHICH ARE USEFUL AS THROMBOXANE A$_2$ ANTAGONISTS

[75] Inventor: David G. Cooper, Letchworth, England

[73] Assignee: Smith Kline & French Laboratories Limited, Welwyn Garden City, England

[21] Appl. No.: 178,663

[22] Filed: Apr. 7, 1988

[51] Int. Cl.$^4$ .......................................... C07D 213/42
[52] U.S. Cl. .................. 514/351; 514/352; 546/293; 546/312
[58] Field of Search ............... 546/293, 312; 514/351, 514/352

[56] References Cited

U.S. PATENT DOCUMENTS 3,341,536 9/1967 Beschke et al. .................... 544/106
4,210,759 7/1980 Virnig ................................. 546/312

FOREIGN PATENT DOCUMENTS 0004011 9/1979 European Pat. Off. ............. 564/80
0031954 7/1981 European Pat. Off. ............. 564/80
194548 9/1986 European Pat. Off. ............. 544/242
0223593 5/1987 European Pat. Off. ............. 564/80
0226346 6/1987 European Pat. Off. ............. 564/80
0239907 10/1987 European Pat. Off. ............. 564/80
0255728 2/1988 European Pat. Off. ............. 564/80
0076996 4/1988 European Pat. Off. ............ 544/336
0262395 4/1988 European Pat. Off. ............ 548/566
3535167 4/1987 Fed. Rep. of Germany ........ 564/80

OTHER PUBLICATIONS

Windholz et al., *The Merck Index*, 10th Ed., 1983, p. 8811, entry 8814.

*Primary Examiner*—Mary C. Lee
*Assistant Examiner*—Zinna Northington-Davis
*Attorney, Agent, or Firm*—Stuart R. Suter; Alan D. Lourie

[57] ABSTRACT

The invention provides a class of alkanoic acids substituted with a benzenesulphonamidopyridyl group. The compounds have activity as thromboxane A$_2$ antagonists.

14 Claims, No Drawings

BENZENESULPHONAMIDOPYRIDYL COMPOUNDS WHICH ARE USEFUL AS THROMBOXANE $A_2$ ANTAGONISTS

The present invention relates to a class of pyridylalkanoic acid compounds containing a sulphonamido group which have activity as thromboxane $A_2$ antagonists, to the use of the compounds in medicine, to pharmaceutical compositions containing them and to methods for their preparation.

Thromboxane $A_2$ ($TXA_2$) is a potent vasoconstricting and platelet aggregating agent which is formed in platelets and other tissues as a product of the "arachidonic acid cascade". $TXA_2$ is produced by the thromboxane synthetase catalysed conversion of prostaglandin $H_2$ ($PGH_2$) which in turn is produced, via the intermediacy of prostaglandin $G_2$ ($PGG_2$), by the action of cyclooxygenase on arachidonic acid. The potency of $TXA_2$ is such that very small amounts can trigger serious biological consequences and it has been implicated in mediating pathophysiological actions in severe disorders such as circulatory shock and myocardial ischaemia.

One method of inhibiting the effects of thromboxane $A_2$ is through the selective antagonism of $TXA_2/PGH_2$ at the receptor level and various compounds have been reported as $TXA_2$ receptor antagonists, see for example U.S. Pat. No. 4,536,510 and U.S. Pat. No. 4,443,477.

It has now been discovered that a class of sulphonamide-substituted pyridylalkanoic acids has biological activity indicative of an ability to antagonise the action of $TXA_2$ at $TXA_2$ receptors. Accordingly, in a first aspect, the present invention provides compounds of the formula (I):

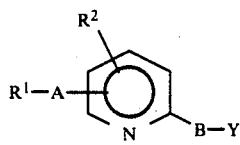

and salts thereof; wherein
A is a group $NR^3SO_2$ or $SO_2NR^3$; B is $C_{1-6}$ alkylene;
Y is $CO_2H$ or a group hydrolysable to $CO_2H$;
$R^1$ is phenyl optionally substituted by one or more substituents chosen from the group comprising halogen, $C_{1-4}$ alkyl, $C_{1-6}$ acyl, $C_{1-4}$ alkoxy, nitro and trifluoromethyl, provided that when $R^1$ is phenyl substituted by two or more substituents, no more than one substituent can be meta-trifluoromethyl;
$R^2$ is hydrogen or one or more $C_{1-4}$ alkyl substituents; and $R^3$ is hydrogen or $C_{1-6}$ alkyl.

The group $R^1$—A can be ortho, meta or para with respect to the nitrogen atom of the pyridine ring. Preferably it is meta to the pyridine nitrogen atom, and particularly preferably it is also para with respect to the group B—Y.

The group Y hydrolysable to $CO_2H$ suitably is a nitrile, amide or ester, for example a $C_{1-4}$ alkoxycarbonyl group such as ethoxycarbonyl or methoxycarbonyl, or a carbamoyl, mono-$C_{1-6}$ alkylcarbamoyl or di-$C_{1-6}$ alkylcarbamoyl group such as N-methylaminocarbonyl and N,N-dimethylaminocarbonyl.

In particular $R^1$ represents an unsubstituted phenyl group or a phenyl group having one or two substituents, preferably in the 3- and/or 4-positions of the phenyl ring.

Examples of $C_{1-6}$ acyl substituents for $R^1$ are $C_{1-6}$ alkanoyl, $C_{1-6}$ alkoxycarbonyl and carbamoyl.

Preferred examples of the group $R^1$ are unsubstituted phenyl or mono-substituted phenyl wherein the substituent is an atom or group in the 3- or 4-position, preferably the 4-position, selected from chloro, bromo, methyl, trifluoromethyl and methoxy, a most preferred example being phenyl substituted with 4-chloro or 4-bromo.

Examples of the group $R^2$ are hydrogen, methyl and ethyl, particularly hydrogen.

Suitably $R^3$ is hydrogen or methyl, particularly hydrogen.

The group B can be a straight chain or branched chain alkylene group but preferably it is a straight chain alkylene group having from two to five carbon atoms, particularly three or four carbon atoms. Examples of straight chain groups are ethane-1,2-diyl, propane-1,3-diyl, butane-1,4-diyl and pentane-1,5-diyl. Examples of branched chain alkylene groups are 2-methylbutane-2,4-diyl and 2-methylpentane-2,5-diyl, the point of attachment of the group Y being at the 2-position. Preferred alkylene groups are propane-1,3-diyl and butane-1,4-diyl, a particularly preferred group being propane-1,3-diyl.

One particular group of compounds of the present invention is represented by the general formula (II):

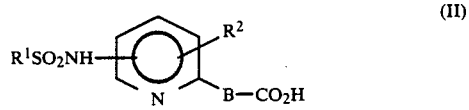

and salts thereof, wherein $R^1$, $R^2$ and B are as defined above.

Particular and preferred groups B, $R^1$ and $R^2$ for compounds of the formula (II) are as defined above in respect of compounds of the formula (I).

Preferably the group $R^1SO_2NH$ is meta to the pyridine ring nitrogen, and particularly preferably it is also para with respect to the group B—$CO_2H$.

Particular compounds of the present invention are
4-(5-benzenesulphonamidopyrid-2-yl)butanoic acid,
4-[5-(4-chlorobenzenesulphonamido)pyrid-2-yl]butanoic acid,
4-(5-benzenesulphonamido-3-methylpyrid-2-yl)butanoic acid,
5-[5-(4-chlorobenzenesulphonamido)pyrid-2-yl]pentanoic acid,
4-[5-(3-chlorobenzenesulphonamido)pyrid-2-yl]butanoic acid,
4-[5-(3,4-dichlorobenzenesulphonamido)pyrid-2-yl]butanoic acid,
4-[5-(4-bromobenzenesulphonamido)pyrid-2-yl]butanoic acid, and
4-[5-(4-methylbenzenesulphonamido)pyrid-2-yl]butanoic acid.

Compounds of the formula (I) can form several different types of salt, for examples acid addition salts, formed by interaction of the nitrogen atom of the pyridine ring with an appropriate proton acid, and salts formed by interaction of the carboxylic acid group and/or the sulphonamido group with an appropriate base. Where compounds of the formula (I) exist in zwitterionic form, such forms are also within the scope of this invention.

Examples of acid addition salts are those formed by interaction of a compound of the formula (I) with an acid selected from hydrochloric, sulphuric, phosphoric, acetic, methanesulphonic, ethanesulphonic, isethionic, glucuronic, lactobionic, toluenesulphonic, benzenesulphonic, naphthalenesulphonic, hydrobromic, tartaric, citric, maleic, lactic, and camphorsulphonic acids.

Examples of carboxylate salts are alkali metal, alkaline earth metal and ammonium salts. Alkali and alkaline earth metal salts typically are formed by interaction of a carboxylic acid with a metal alkoxide or hydroxide whereas ammonium salts typically are formed by interaction of the carboxylic acid with the appropriate amine or the appropriate ammonium hydroxide.

It is preferred that the salts are pharmaceutically acceptable, although non-pharmaceutical salts are also within the scope of the invention. Such salts can be converted into pharmaceutically acceptable salts or into the corresponding free base or free acid.

Where the compounds of formula (I) exist as solvates, for examples hydrates and alcoholates, such forms are also within the scope of the invention.

Compounds of the formula (I) wherein Y is $CO_2H$ have activity as thromboxane $A_2$ receptor antagonists. Compounds of the formula (I) wherein Y is a group hydrolysable to $CO_2H$ are primarily useful as chemical intermediates, unless they are metabolised by mammals to compounds wherein Y is $CO_2H$ in which case they can function as pro-drugs.

Compounds of the formula (I) can be prepared by the reaction of a compound of the formula (III):

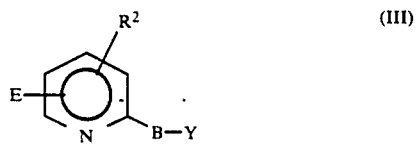

(III)

wherein E is amino or a group $SO_2L$;
$R^2$ is as defined above; and
L is a leaving group displaceable by amino;
with a compound of the formula $R^1M$ wherein M is amino or a group $SO_2L$, provided that one of E and M is $SO_2L$ and the other is amino; and thereafter, where necessary, hydrolysing Y to give $CO_2H$.

Examples of leaving groups L are the halogens, particularly chlorine.

The reaction of compounds of the formula (III) with compounds of the formula $R^1M$ can be conducted under conditions known for the preparation of analogous sulphonamides. Thus, for example, the reaction can be conducted in a solvent, for example benzene, toluene or a polar solvent such as acetone, acetonitrile, a halogenated hydrocarbon such as dichloromethane or a basic solvent such as pyridine, with heating where required, for example at the reflux temperature of the solvent. Where the solvent is non-basic the reaction typically is conducted in the presence of a base such as pyridine or a trialkylamine such as triethylamine.

Alternatively, the reaction can be conducted under Schotten-Baumann conditions, i.e. the reactants are stirred or shaken together in the presence of an aqueous alkali such as dilute sodium hydroxide.

Compounds of the formula (III) wherein E is amino can be prepared from a compound of the formula (IV):

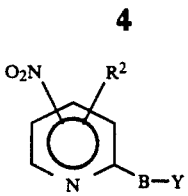

(IV)

by treatment with an appropriate reducing agent, for example by hydrogenating over a transition metal catalyst such as palladium on charcoal, or by treatment with hydrazine in the presence of palladium on charcoal. Suitable solvents for use in such reactions are $C_{1-4}$ alkanols such as methanol and ethanol and typically the reaction is conducted at approximately ambient temperature.

Compounds of the formula (IV) can be prepared by the reaction of a compound of the formula (V):

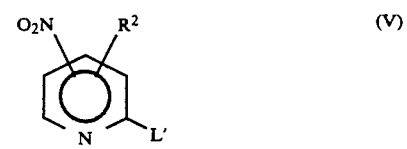

(V)

wherein L' is a leaving group, with a metal derivative of a compound $H-B^1-Y$ wherein $B^1$ is a group B optionally substituted by one or more anion-stabilising groups, and thereafter removing any anion-stabilising groups. Suitable leaving groups L' will be apparent to those skilled in the art and include, for example, a halogen, e.g. chlorine.

By anion-stabilising group is meant a removable group adjacent to the terminal carbon atom of the group $H-B-Y$ which increases the acidity of the group and which subsequently exerts a stabilising influence of an anion $\ominus B^1-Y$. Examples of such removable groups are alkoxycarbonyl groups such as ethoxycarbonyl.

Examples of compounds of the formula $H-B^1-Y$ containing anion-stabilising groups are compounds of the formula

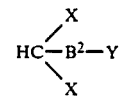

wherein X is cyano or $C_{1-4}$ alkoxycarbonyl and $B^2$ is a bond or a $C_{1-5}$ alkylene group. A particular example of such a group is $HC(CO_2Et)_2B^2-Y$. The metal typically is an alkaline metal such as lithium, sodium or potassium and usually it is sodium.

The reaction of a compound of the formula (V) with the metal derivative of the compound $H-B^1-Y$ can be carried out in a polar solvent, for example, ethers such as diethyl ether and tetrahydrofuran, or dimethylsulphoxide, with heating where necessary; for example to the reflux temperature of the solvent. Metal derivatives of compounds of the formula $H-B^1-Y$ can be formed according to conventional methods, for example by reacting the compound with elemental metal, or a strong base containing the metal, such as the metal hydride.

Compounds of the formula (III) wherein E is a group $SO_2Cl$ can be prepared by diazotisation of the corresponding compound wherein E is $NH_2$ with sodium nitrite and hydrochloric acid followed by treatment with sulphur dioxide in acetic acid in the presence of a copper catalyst such as Cu(I)Cl or Cu(II)Cl$_2$—see for example E. E. Gilbert. *Synthesis*. 1969, 6.

When the group Y is a group hydrolysable to CO$_2$H, the hydrolysis conditions employed will depend upon the precise nature of the group, but generally the hydrolysis is achieved by treating with either an aqueous mineral acid such as hydrochloric or sulphuric acids or an alkali such as sodium hydroxide, with heating as required.

Compounds of the formula (I) are useful in the treatment of diseases in which TXA$_2$ is a factor. Thus they would be useful in the treatment of disorders in which aggregation of blood platelets and vasoconstriction play a part.

Particular clinical indications in which the present compounds would be of interest include the treatment or management of post myocardial infarction, coronary thromboses (e.g. in combination with tissue plasminogen activator and other thrombolytics), unstable angina, transient ischaemia, coronary artery bypass grafts, cardiac valve replacement and peripheral and vascular grafts including for example renal transplants.

The compounds of the formula (I) can be administered as the pure compound but it is more usual to administer them as part of a pharmaceutical composition in association with a carrier and one or more excipients. In a further aspect, therefore, the present invention provides a pharmaceutical composition comprising a compound of the formula (I) and a pharmaceutically acceptable carrier.

The compositions can be administered in standard manner, for example orally, parenterally, transdermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil. Such compositions can be administered, for example, by bolus injection or by infusion.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each such dosage unit suitably contains from 1 mg to 1 g, preferably from 5 mg to 500 mg. e.g. 100 mg or 200 mg, of a compound of the formula (I) or a pharmaceutically acceptable salt thereof calculated as the compound itself.

A typical daily dosage regimen is 10 mg to 1 g for an average human weighing approximately 70 kg, administered in 1 to 4 dosage units, preferably 1 to 2.

The compositions of this invention, in addition to containing a compound of the formula (I) can also contain other agents; for example one or more agents chosen from phosphodiesterase inhibitors, hypolipidemic agents, platelet aggregation inhibitors, vasodilators, β-adrenergic receptor blockers, ACE inhibitors, tissue plasminogen activator and other thrombolytics, and antiarrhythmics.

The compositions of the present invention are prepared by bringing the active constituent into association with a pharmaceutically acceptable carrier and optionally other excipients and ingredients as defined above.

As indicated above, compounds of the formula (I) have biological activity that is indicative of an ability to antagonise TXA$_2$ receptors. The TXA$_2$ activity has been demonstrated in the human platelet binding assay.

The platelet binding assay used was essentially the method described by Mais et al. *J. Pharm. Exp. Ther.*, 1985, 235(3), 729–734 where [$^{125}$I]PTA-OH was used as the receptor ligand.

The IC$_{50}$ values represent the concentration which produces a 50% inhibition of specific [$^{125}$I]PTA-OH binding.

The following Examples are illustrative of the invention.

In the Examples, all temperatures are in ° C. Melting points are uncorrected and were obtained in an open capillary tube using a Büchi 510 Melting Point Apparatus.

EXAMPLE 1

(a) Diethyl 2-(2-cyanoethyl)-2-(5-nitropyrid-2-yl)malonate

Sodium hydride (53% dispersion in oil) (30.71 g, 0.66 mole) was washed by decantation with xylene (2×150 ml), ether (150 ml), tetrahydrofuran (THF) (150 ml) and finally suspended in THF (245 ml). Diethyl 2-(2-cyanoethyl) malonate (156 g, 0.73 mole) in THF (80 ml) was added dropwise over 1 hr keeping the internal temperature at 18° C. to 22° C. (with ice bath cooling). The resulting suspension cleared over 15 minutes when 2-chloro-5-nitropyridine (88.3 g, 0.55 mole) was added to give a deep magenta solution. The resulting solution was refluxed for 1 hr and the solvent was removed on the rotary evaporator. The resulting oil was partitioned between water (500 ml) and chloroform (800 ml), the pH was adjusted to ~7 (concentrated hydrochloric acid), and the chloroform was run off. The aqueous layer was extracted with a further (2×250 ml) chloroform, the extracts were combined, dried over magnesium sulphate and the solvent was removed to give an amber oil (~245 g). Ether (150 ml) was added and the solution was allowed to crystallise to give the title compound (121.98 g, 65%), m.p. 59.5°–61° C.

(Found C, 53.7; H. 5.05; N, 12.35%. $C_{15}H_{17}N_3O_6$ requires C, 53.75; H, 5.1; N, 12.55%) NMR (CDCl$_3$, 60 MHz); δ 1.37 (6 H, t); 2.65 (4 H, m); 4.26 (4 H, q); 7.84 (1 H, dd); 8.49 (1 H, dd); 9.32 (1 H, dd).

(b) 4-(5-nitropyrid-2-yl)butanoic acid

A solution of diethyl 2-(2-cyanoethyl)-2-(5-nitropyrid-2-yl)malonate (50 g, 0.15 mole) in 48% w/v hydrobromic acid (200 ml) was refluxed for 2 hours. The pH of the solution was adjusted to pH=2 with 40% w/v sodium hydroxide solution. The resulting solution was extracted with chloroform (3×200 ml). The combined chloroform extracts were dried over magnesium sulphate, evaporated to dryness and the residue was treated with charcoal in ethanol and recrystallised from ethanol to give the title compound (24.94 g) as white needles. m.p. 108°–110° C.

(c) Methyl 4-(5-aminopyrid-2-yl)butanoate

Hydrazine hydrate (10 ml) in ethanol (20 ml) was added over 30 minutes to a stirred suspension of 4-(5-nitropyrid-2-yl)butanoic acid (7.5 g, 0.036 mole) and 10% palladium on carbon (1 g) in ethanol (100 ml). The solution was stirred for 1 hour, filtered through hyflo and the filtrate was evaporated to dryness. The residue was dissolved in methanol (250 ml) containing concentrated sulphuric acid (20 ml) and the resulting solution was refluxed for 4 hours, cooled and the solvent was removed under reduced pressure. The residue was dissolved in water (100 ml), basified and extracted with chloroform (3×100 ml). The chloroform extracts were combined, dried over magnesium sulphate, and evaporated to dryness. The residue was distilled in a kugelrohr apparatus (oven temp. 145° C. at 0.05 mmHg) to give the title compound 3.84 g as a straw coloured oil.

(d) Methyl 4-(5-Benzenesulphonamidopyrid-2-yl)butanoate

Triethylamine (1 ml) in chloroform (10 ml) was added over 10 minutes to a solution of methyl 4-(5-aminopyrid-2-yl)-butanoate (1.5 g, 8.3 mmole) and benzene sulphonyl chloride (2.2 g, 12 mmole) in chloroform (20 ml). The solution was stirred for 4 hours. Chromatography on silica gel eluted with 5% v/v methanol in chloroform gave the title compound (1.46 g) as a straw coloured oil.

(e) 4-(5-Benzenesulphonamidopyrid-2-yl)butanoic acid

A solution of methyl 4-(5-benzenesulphonamidopyrid-2-yl)-butanoate (1.3 g, 4.2 mmole) in ethanol (25 ml) and 10% w/v sodium hydroxide solution (10 ml) was stirred for 1 hour. The solution was treated with hydrochloric acid and the precipitate was collected by filtration.

Recrystallisation from ethanol gave the title compound (0.94 g) as white needles. m.p. 181°–182° C.

(Found: C, 56.18; H, 5.05; N, 8.74; S, 10.13%, $C_{15}H_{16}N_2O_4S$ requires C, 56.23; H, 5.03; N, 8.74; S, 10.0%).

EXAMPLE 2

(a) 4-(5-Aminopyrid-2-yl)butanoic acid

A mixture of 4-(nitropyrid-2-yl)butanoic acid (15 g) and 10% palladium on carbon (1.5 g) in methanol (250 ml) was shaken under an atmosphere of hydrogen at 50 p.s.i. until uptake of hydrogen was complete. The catalyst was removed by filtration and filtrate was evaporated to dryness. The residue was recrystallised from acetonitrile to give the title compound as cream coloured needles (11.27 g). m.p. 101°–102° C.

(b) 4-[5-(4-Chlorobenzenesulphonamido)pyrid-2-yl]-butanoic acid

4-Chlorobenzenesulphonyl chloride (1.17 g) was added portionwise to a solution of 4-(5-aminopyrid-2-yl)butanoic acid (1 g) in pyridine (15 ml). The resulting solution was allowed to stand at room temperature overnight when the solvent was removed under reduced pressure. The residue was dissolved in dilute sodium hydroxide solution (50 ml) and extracted with chloroform (4×50 ml) and the chloroform extracts were discarded. The aqueous layer was adjusted to pH=4 and was extracted with chloroform (3×100 ml). The chloroform extracts were dried over magnesium sulphate, the solvent was removed and residue was recrystallised from acetonitrile/water 1:1 to give the title compound (0.7 g) as white plates. m.p. 178°–180° C.

Anal. Found: C=50.97, H=4.32, N=7.82, Cl=9.99, S=8.76%, $C_{15}H_{15}ClN_2O_4S$ requires: C=50.78, H=4.26, N=7.90, Cl=9.99, S=8.76%.

NMR (250 MHz) (d$^6$-dimethylsulphoxide) δ (ppm) 1.82 (2 H, m); 2.19 (2 H, m), 2.62 (2 H, m) 7.15 (1 H, d), 7.40 (1 H, dd), 7.63 (1 H, m), 7.66 (1 H, m), 8.16 (1 H, m).

Infra Red (nujol mull) ν (cm$^{-1}$) 3088, 2430, 1669, 1608.

EXAMPLE 3

(a) 5-Benzenesulphonamido-2-(3-cyanopropyl)-3-methylpyridine

A solution of 5-amino-2-(3-cyanopropyl)-3-methylpyridine* (5 g) in chloroform (50 ml) was treated with benzenesulphonyl chloride (7.35 ml) and triethylamine (3 ml) for 96 hours. The chloroform layer was extracted with dilute sodium hydroxide solution (2×50 ml). The chloroform layer was discarded and the combined aqueous extracts were adjusted to pH=5 and extracted with chloroform (3×50 ml). The combined extracts were dried over magnesium sulphate, the solvent was removed and the residue was chromatographed on silica gel eluted with 2% v/v methanol in chloroform to give the title compound (3.28 g) as white prisms. m.p. 119°–120° C.

* see Example 1 of U.S. 4,486,434.

(b) 4-(5-Benzenesulphonamido-3-methylpyrid-2-yl)butanoic acid

A solution of 5-benzenesulphonamido-2-(3-cyanopropyl)-3-methylpyridine (1.5 g) in ethanol (100 ml) and 15% w/v sodium hydroxide solution (20 ml) was refluxed for 8 hours. The ethanol was removed under reduced pressure and the pH of the remaining aqueous was adjusted to pH 4 when a white solid crystallised. The solid was collected and recrystallised from methanol to give the title compound (0.7 g) as white needles. m.p. 169°-179° C.

EXAMPLE 4

(a) 3-Benzenesulphonamido-2-(3-cyanopropyl)pyridine

A solution of 3-amino-2-(3-cyanopropyl)pyridine* (5 g, 0.031 mole) in acetonitrile (50 ml) was treated with benzenesulphonyl chloride (4 ml) and pyridine (6 ml). The solution was allowed to stand at room temperature overnight when the solvent was removed in vacuo. The residue was dissolved in dilute sodium hydroxide (100 ml) and was extracted with chloroform (4×100 ml) the chloroform extracts being discarded. The aqueous layer was adjusted to pH=4 and extracted with chloroform (3×100 ml). The combined chloroform extracts were dried over magnesium sulphate, the solvent was removed to give the title compound (7.12 g) as a cream coloured solid. m.p. 80°-81° C.
* see Example 13 of U.S. Pat. No. 4,154,834

(b) 4-(3-Benzenesulphonamidopyrid-2-yl)butanoic acid

A solution of 3-benzenesulphonamido-2-(3-cyanopropyl)pyridine (5.22 g) in ethanol (100 ml) and 15% w/v sodium hydroxide solution (50 ml) was refluxed for 6 hours. The pH of the solution was adjusted to pH=4 when a white solid precipitated from the solution. The solid was collected by filtration and recrystallised from ethanol to give the title compound (3.34 g) as white needles. m.p. 156°-157° C.

EXAMPLE 5

4-[5-(3-Chlorobenzenesulphonamido)pyrid-2-yl]butanoic acid

A solution of 3-chlorobenzenesulphonyl chloride (1.17 g), dissolved in 5 ml pyridine, was added dropwise to a solution of 4-(5-aminopyrid-2-yl)butanoic acid (1 g) in pyridine (10 ml). The resulting solution was allowed to stand at room temperature overnight when the solvent was removed under reduced pressure. The residue was taken up in dilute sodium hydroxide solution (40 ml) and extracted with chloroform (4×50 ml) the chloroform extracts were discarded. The aqueous layer was adjusted to pH 4 with hydrochloric acid, extracted with chloroform (3×100 ml) and then ethyl acetate (2×100 ml). Chloroform and ethyl acetate extracts were dried over magnesium sulphate, solvents removed and residue recrystallised from acetonitrile/water to give the title compound (1.29 g) as a white solid. m.p. 141°-142° C.

EXAMPLE 6

(a) Diethyl 2-(3-cyanopropyl)-2-(5-nitropyrid-2-yl)malonate

Sodium hydride (50% dispersion in oil) (5.85 g, 0.12 mole) was washed by decantation with hexane (2×150 ml), tetrahydrofuran (THF) (100 ml) and was finally suspended in THF (160 ml). Diethyl 2-(3-cyanopropyl) malonate (30 g, 0.13 mole) in THF (20 ml) was added dropwise over 45 minutes keeping the internal temperature at 18° C. to 22° C. (with ice bath cooling). The resulting suspension cleared over 30 min when 2-chloro-5-nitropyridine (16.1 g, 0.1 mole) was added to give a deep magenta solution. The resulting solution was refluxed for 1 hr and the solvent was removed on the rotary evaporator. The resulting oil was partitioned between water (100 ml) and chloroform (200 ml), the pH was adjusted to ~7 (concentrated hydrochloric acid), and the chloroform was run off. The aqueous layer was extracted with a further (2×250 ml) chloroform, the extracts were combined, dried over magnesium sulphate and the solvent was removed to give the title compound as an amber oil (42.53 g) which was used without further purification.

(b) 5-(5-Nitropyrid-2-yl)pentanoic acid

A solution of diethyl 2-(3-cyanopropyl)-2-(5-nitropyrid-2-yl)malonate (42.53 g, 0.1 mole) in 48% w/v hydrobromic acid (165 ml) was refluxed for 3 hours. The pH of the solution was adjusted to pH=3 with 40% w/v sodium hydroxide solution. The resulting solution was extracted with chloroform (3×200 ml). The combined chloroform extracts were dried over magnesium sulphate, evaporated to dryness and the residue was treated with charcoal in ethanol and recrystallised from ethanol to give the title compound (12.12 g) as white needles. m.p. 105°-107° C.

(c) 5-(5-Aminopyrid-2-yl)pentanoic acid

A solution of 5-(5-nitropyrid-2-yl)pentanoic acid (6.0 g) in ethanol (140 ml) containing 10% palladium on carbon (0.6 g) was shaken under an atmosphere of hydrogen at 3.4 atmospheres pressure for 1 hour. The catalyst was removed by filtration, the filtrate was evaporated to dryness and the residue was recrystallised from acetonitrile to give the title compound as a cream coloured solid (4.04 g). m.p. 80°-82° C.

(d) 5-[5-(4-Chlorobenzenesulphonamido)pyrid-2-yl]pentanoic acid

4-Chlorobenzenesulphonyl chloride (1.09 g, 5.15 mmole) was added portionwise over 10 minutes to a solution of 5-(5-aminopyrid-2-yl)pentanoic acid (1.00 g, 5.15 mmole) in pyridine (15 ml). The resulting solution was stirred for 18 hours when the solvent was removed and the residue was dissolved in dilute sodium hydroxide solution (30 ml). This solution was extracted with ethyl acetate (4×50 ml) the extracts being discarded. The aqueous layer was acidified (pH 3) and extracted with ethyl acetate (4×100 ml). The combined ethyl acetate extracts were dried over magnesium sulphate, evaporated to dryness and the residue was recrystallised from acetonitrile to give the title compound (1.21 g) as a pale yellow solid. m.p. 145°-147° C.

EXAMPLE 7

5-[5-(Benzenesulphonamido)pyrid-2-yl]pentanoic acid

Substituting benzenesulphonyl chloride (0.91 g, 5.15 mmole) for 4-chlorobenzenesulphonyl chloride in the method described in Example 6 gave the title compound (0.99 g). m.p. 136°-138° C.

EXAMPLE 8

(a) Diethyl 2-(cyanomethyl)-2-(5-nitropyrid-2-yl)malonate

Sodium hydride (53% dispersion in oil) (5.17 g, 0.1 mole) was washed by decantation with hexane (2×150 ml), tetrahydrofuran (THF) (150 ml) and was finally suspended in THF (150 ml). Diethyl 2-(cyanomethyl)-malonate (26.4 g, 0.11 mole) in THF (20 ml) was added dropwise over 45 minutes keeping the internal temperature at 18° C. to 22° C. (with ice bath cooling). The resulting suspension cleared over 15 minutes when 2-chloro-5-nitropyridine (14.22 g, 0.09 mole) was added to give a deep magenta solution. The resulting solution was refluxed for 3 hours and the solvent was removed on the rotary evaporator. The resulting oil was partitioned between water (200 ml) and chloroform (200 ml), the pH was adjusted to ~7 (concentrated hydrochloric acid), and the chloroform was run off. The aqueous layer was extracted with a further (2×250 ml) chloroform, the extracts were combined, dried over magnesium sulphate and the solvent was removed to give the title compound as an amber oil. Ether (25 ml) was added and the solution was allowed to crystallise to give the title compound (18.48 g). m.p. 66°–68° C.

(b) 3-(5-Nitropyrid-2-yl)propionic acid

A solution of diethyl 2-(cyanomethyl)-2-(5-nitropyrid-2-yl)malonate (18.44 g, 0.057 mole) in 48% w/v hydrobromic acid (100 ml) was refluxed for 3.5 hours. The pH of the solution was adjusted to pH=3 with 40% w/v sodium hydroxide solution. The resulting solution was extracted with chloroform (3×200 ml). The combined chloroform extracts were dried over magnesium sulphate, evaporated to dryness and the residue was recrystallised from ethanol to give the title compound (8.24 g). m.p. 126°–128° C.

(c) 3-(5-Aminopyrid-2-yl)propionic acid

A solution of 3-(5-nitropyrid-2-yl)propionic acid (4.50 g) in ethanol (140 ml) containing 10% palladium on carbon (0.45 g) was shaken under an atmosphere of hydrogen at 3.4 atmospheres pressure for 1.5 hours. The catalyst was removed by filtration and the filtrate was evaporated to dryness. The residue was recrystallised from acetonitrile to give the title compound (3.43 g) m.p. 118°–120° C.

(d) 3-[5-(4-Chlorobenzenesulphonamido)pyrid-2-yl]propionic acid

A solution of 3-(5-aminopyrid-2-yl)propionic acid (1.00 g) and 4-chlorobenzenesulphonyl chloride (1.27 g) in pyridine (15 ml) was stirred at room temperature overnight. The solvent was removed and the residue was dissolved in dilute sodium hydroxide (30 ml) and extracted with chloroform (4×50 ml). The aqueous layer was acidified with dilute hydrochloric acid (pH 3) and extracted with ethyl acetate (4×100 ml). The ethyl acetate extracts were combined, dried over magnesium sulphate, the solvent was removed and the residue was recrystallised from acetonitrile to give the title compound (1.30 g). m.p. 144°–146° C.

EXAMPLE 9

(a) Methyl 4-(5-chlorosulphonylpyrid-2-yl)butanoate

Sodium nitrite (6.08 g) in water (12 ml) was added over 20 minutes to a solution of methyl 4-(5-aminopyrid-2-yl)butanoate (7.48 g, 0.04 mole) in glacial acetic acid (20 ml) and concentrated hydrochloric acid (32 ml) stirred at −10° C. The solution was stirred for 15 minutes then added over 15 minutes to a solution of cuprous chloride (2 g) in glacial acetic acid saturated with sulphur dioxide at 10° C. The resulting solution was stirred at room temperature for 1 hour then poured into ice water (250 ml) and extracted with chloroform (3×200 ml). The chloroform extracts were dried over magnesium sulphate and the solvent was removed to give the title compound as a pale green oil which was used without further purification.

(b) Methyl 4-[5-(4-chlorophenylsulphamoyl)pyrid-2-yl]butanoate

A mixture of methyl 4-(5-chlorosulphonylpyrid-2-yl)butanoate (2.5 g), 4-chloroaniline (1.9 g) and pyridine (10 ml) was allowed to stand at room temperature overnight. The solvent was removed in vacuo and the residue was dissolved in water, acidified (pH 3) and extracted with chloroform (3×25 ml). The chloroform extracts were dried over magnesium sulphate, the solvent was removed and the residue was chromatographed on silica gel, eluting with chloroform, and recrystallised from chloroform/hexane to give the title compound (1.26 g) as white needles. m.p. 80°–81° C.

(c) 4-[5-(4-Chlorophenylsulphamoyl)pyrid-2-yl]-butanoic acid

A solution of methyl 4-[5-(4-chlorophenylsulphamoyl)pyrid-2-yl]butanoate (0.8 g), 10% w/v sodium hydroxide solution (5 ml) in ethanol (15 ml) was stirred for 1 hour. The solution was acidified with dilute hydrochloric acid (pH 3) and cooled to 5° C. The white precipitate was collected and recrystallised from ethanol to give the title compound (0.504 g) as prisms. m.p. 150°–152° C.

Anal. Found C=50.78, H=4.31, N=7.88, Cl=10.09, S=8.85%, $C_{15}H_{15}ClN_2O_4S$ requires C=50.78, H=4.26, N=7.90, Cl=9.99, S=9.04%.

EXAMPLE 10

(a) Methyl 4-[5-(phenylsulphamoyl)pyrid-2-yl]butanoate

Substituting aniline (1.4 g) in the previous example gave the title compound (1.17 g) as needles from chloroform/hexane, m.p. 79°–80° C.

(b) 4-[5-(Phenylsulphamoyl)pyrid-2-yl]butanoic acid

A solution of methyl 4-[5-(phenylsulphamoyl)pyrid-2-yl]butanoate (0.7 g), 10% w/v sodium hydroxide solution (5 ml) in ethanol (10 ml) was stirred for 1 hour. The solution was acidified with dilute hydrochloric acid (pH=3) and cooled. The precipitate was collected and recrystallised from ethanol to give the title compound as prisms (0.56 g). m.p. 158°–159° C.

Anal. Found C=56.02, H=5.08, N=8.67, S=10.14%, $C_{15}H_{16}N_2O_4S$ requires C=56.24, H=5.03, N=8.74, S=10.01%.

EXAMPLE 11

4-[5-(4-Methoxybenzenesulphonamido)pyrid-2-yl]butanoic acid

A solution of 4-methoxybenzenesulphonyl chloride (2.06 g) and 4-(5-aminopyrid-2-yl)butanoic acid (1.8 g) in pyridine (15 ml) was allowed to stand at room temperature for 18 hours. The solvent was removed and the residue was dissolved in water and treated with dilute hydrochloric acid to give a solution at pH 4.5. The resulting precipitate was collected and recrystallised from ethanol to give the title compound (1.96 g) as prisms. m.p. 129°–130° C.

Anal. Found: C=55.06, H=5.15, N=8.06, S=9.01%, $C_{16}H_{18}N_2O_5S$ requires: C=54.84, H=5.18, N=8.00, S=9.15%.

EXAMPLE 12

4-[5-(3-Trifluoromethylbenzenesulphonamido)-pyrid-2-yl]butanoic acid

Substituting 3-trifluoromethylbenzenesulphonyl chloride (2.44 g) in Example 11 gave the title compound (2.37 g) as prisms from ethanol water. m.p. 157°–159° C.

Anal. Found: C=49.59, H=3.95, N=7.22, S=8.33%, $C_{16}H_{15}F_3N_2O_4S$ requires: C=49.48, H=3.89, N=7.21, S=8.25%.

EXAMPLE 13

4-[5-(4-Bromobenzenesulphonamido)pyrid-2-yl]butanoic acid

Substituting 4-bromobenzenesulphonyl chloride (2.55 g) in Example 11 gave the title compound (2.27 g) as prisms from ethanol. m.p. 188°–190° C.

Anal. Found: C=45.17, H=3.89, N=6.86, Br=19.96, S=7.78%, $C_{15}H_{15}N_2BrO_4S$ requires: C=45.12, H=3.79, N=7.02, Br=20.01, S=8.03%.

EXAMPLE 14

4-[5-(4-Methylbenzenesulphonamido)pyrid-2-yl]butanoic acid

Substituting 4-toluenesulphonyl chloride (1.90 g) in Example 11 gave the title compound (2.57 g) as prisms from ethanol. m.p. 154°–155° C.

Anal. Found: C=57.34, H=5.42, N=8.29, S=9.43%, $C_{16}H_{18}N_2O_4S$ requires: C=57.47, H=5.43, N=8.38, S=9.59%.

EXAMPLE 15

4-[5-(3,4-Dichlorobenzenesulphonamido)pyrid-2-yl]butanoic acid

Substituting 3,4-dichlorobenzenesulphonyl chloride (1.47 g) in Example 11 gave the title compound (1.80 g) as prisms. m.p. 193°–194° C.

Anal. Found: C=46.21, H=3.58, N=6.97, Cl=18.09, S=7.78%, $C_{15}H_{14}N_2ClO_4S$ requires: C=46.28, H=3.60, N=7.19, Cl=18.22, S=8.23%.

EXAMPLE 16

Biological Activity

The compounds of Examples 1 and 5 were tested in the human platelet binding assay. The results obtained are shown in the Table below:

| Compound of Example No. | Human Platelet Binding $IC_{50}(\mu m)$ |
|---|---|
| 1 | 1.3 |
| 2 | 0.36 |
| 3 | 2.6 |
| 4 | 102.0 |
| 5 | 1.2 |
| 6 | 1.0 |
| 7 | 4.0 |
| 8 | 251.0 |
| 9 | 21.0 |
| 10 | 28.0 |
| 11 | 5.2 |
| 12 | 16.0 |
| 13 | 0.2 |
| 14 | 0.6 |
| 15 | 2.1 |

We claim:

1. A compound of the formula (I):

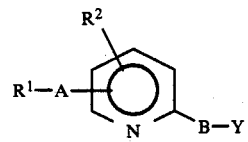

and salts thereof; wherein
A is a group $NR^3SO_2$ or $SO_2NR^3$; B is $C_{1-6}$ alkylene;
Y is $CO_2H$, CN, $C_{1-4}$ alkoxycarbonyl, carbamoyl, mono-$C_{1-6}$ alkylcarbamoyl or di-$C_{1-6}$ alkylcarbamoyl;
$R^1$ is unsubstituted phenyl or phenyl substituted by one or more substituents chosen from the group consisting of halogen, $C_{1-4}$ alkyl, $C_{1-6}$ acyl, $C_{1-4}$ alkoxy, nitro and trifluoromethyl, provided that when $R^1$ is phenyl substituted by two or more substituents, no more than one substituent can be meta-trifluoromethyl;
$R^2$ is hydrogen or one or more $C_{1-4}$ alkyl substituents; and $R^3$ is hydrogen or $C_{1-6}$ alkyl.

2. A compound according to claim 1 wherein Y is $CO_2H$.

3. A compound according to claim 1 wherein $R^3$ is hydrogen or methyl.

4. A compound according to claim 1 having the formula (II):

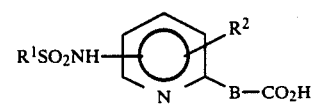

and salts thereof, wherein $R^1$, $R^2$ and B are as defined in claim 1.

5. A compound according to claim 4 wherein $R^1$ is chosen from unsubstituted phenyl or mono-substituted phenyl, wherein the substituent is attached to the 3- or 4-position of the phenyl ring and is chosen from chloro, bromo, methyl, trifluoromethyl and methoxy.

6. A compound to according to claim 4 wherein B is selected from propane-1,3-diyl and butane-1,4-diyl.

7. A compound according to claim 6 wherein B is propane-1,3-diyl.

8. A compound according to claim 1 which is 4-(5-benzenesulphonamidopyrid-2-yl)butanoic acid,
4-[5-(4-chlorobenzenesulphonamido)pyrid-2-yl]butanoic acid
4-(5-benzenesulphonamido-3-methylpyrid-2-yl)butanoic acid,
5-[5-(4-chlorobenzenesulphonamido)pyrid-2-yl]pentanoic acid,
4-[5-(3-chlorobenzenesulphonamido)pyrid-2-yl]butanoic acid,
4-[5-(3,4-dichlorobenzenesulphonamido)pyrid-2-yl]butanoic acid,
4-[5-(4-bromobenzenesulphonamido)pyrid-2-yl]butanoic acid, or
4-[5-(4-methylbenzenesulphonamido)pyrid-2-yl]butanoic acid.

9. A pharmaceutical composition having use in the treatment of diseases mediated by thromboxane $A_2$ comprising a pharmaceutically acceptable carrier and a non-toxic therapeutically effective amount of a compound as defined in claim 2.

10. A pharmaceutical composition having use in the treatment of diseases mediated by thromboxane $A_2$ comprising a pharmaceutically acceptable carrier and a non-toxic therapeutically effective amount of a compound as defined in claim 4.

11. A pharmaceutical composition having use in the treatment of diseases mediated by thromboxane $A_2$ comprising a pharmaceutically acceptable carrier and a non-toxic therapeutically effective amount of a compound as defined in claim 8.

12. A method of treating diseases mediated by thromboxane $A_2$ which comprises administering to a patient in need thereof a non-toxic therapeutically effective amount of a compound as defined in claim 2.

13. A method of treating diseases mediated by thromboxane $A_2$ which comprises administering to a patient in need thereof a non-toxic therapeutically effective amount of a compound as defined in claim 4.

14. A method of treating diseases mediated by thromboxane $A_2$ which comprises administering to a patient in need thereof a non-toxic therapeutically effective amount of a compound as defined in claim 8.

* * * * *